United States Patent [19]

Grenner

[11] Patent Number: 5,147,609
[45] Date of Patent: Sep. 15, 1992

[54] ASSAY ELEMENT

[75] Inventor: Gerd Grenner, Lincoln, Mass.

[73] Assignee: PB Diagnostic Systems, Inc., Westwood, Mass.

[21] Appl. No.: 354,026

[22] Filed: May 19, 1989

[51] Int. Cl.⁵ ............... G01N 31/22; G01N 33/53; G01N 21/77
[52] U.S. Cl. .................... 422/58; 422/56; 422/57; 435/7.1; 435/7.92; 435/7.94; 435/970; 436/170; 436/169; 436/808
[58] Field of Search ............ 422/56, 57, 58, 101, 422/102, 104, 60; 436/47, 48, 170, 808, 169; 435/7.1, 7.92, 7.93, 7.94, 7.95, 975, 970

[56] References Cited

U.S. PATENT DOCUMENTS

| | | | |
|---|---|---|---|
| 3,888,629 | 6/1975 | Bagshawe | 23/230 B |
| 4,517,288 | 5/1985 | Giegel et al. | 435/7 |
| 4,582,684 | 4/1986 | Vogel et al. | 422/57 |
| 4,623,461 | 11/1986 | Hossom et al. | 210/445 |
| 4,761,381 | 8/1988 | Blatt et al. | 422/57 |
| 4,818,677 | 4/1989 | Hay-Kaufman et al. | 435/4 |
| 4,849,340 | 7/1989 | Oberhardt | 435/7.1 |
| 4,857,453 | 8/1989 | Ullman et al. | 435/810 |
| 4,918,025 | 4/1990 | Grenner | 422/56 |
| 4,943,522 | 7/1990 | Eisinger et al. | 422/56 |
| 4,963,498 | 10/1990 | Hillman et al. | 422/102 |
| 4,965,047 | 10/1990 | Hammond | 422/56 |
| 4,988,627 | 1/1991 | Smith-Lewis | 422/56 |
| 5,006,309 | 4/1991 | Khalil et al. | 422/58 |
| 5,006,464 | 4/1991 | Chu et al. | 422/56 |

FOREIGN PATENT DOCUMENTS 0217403 8/1987 European Pat. Off. .
0306336 3/1989 European Pat. Off. .

Primary Examiner—Robert J. Warden
Assistant Examiner—T. A. Trembley
Attorney, Agent, or Firm—Gaetano D. Maccarone

[57] ABSTRACT

There is described an assay element suitable for use in an automated analytical test instrument for assaying a fluid sample. The element includes a thin porous member possessing a high degree of capillarity such as a fibrous mesh pad supported within a guide defined by surfaces contiguous the porous member. The dimensions of the porous member and its degree of capillarity are such as to provide for capillary transport of fluid through the member. A fluid dispenser and a fluid collecting chamber are disposed contiguous to opposed ends of the porous member. The fluid dispenser is formed as a well with a port at the bottom of the well, the port being contiguous the porous member and having a ridge extending along a perimeter of the port. The ridge protrudes into the porous member a distance sufficient for entraining fluid present in the well to propagate within the member rather than along an interface between a surface of the member and guide surfaces which hold it in place. Reservoirs may also be provided in the housing for storing reagents, mixing fluids and diluting samples so as to provide a self contained assay element. Optionally, and preferably, there may be an opening in the housing to provide fluid access directly to the central area of the porous member.

20 Claims, 4 Drawing Sheets

ASSAY ELEMENT

BACKGROUND OF THE INVENTION

The invention relates to assay elements suitable for use in automated analytical test systems and, more particularly, to an assay element which includes a thin porous member.

Various types of chemical tests can be performed by automated test equipment, an example of testing of considerable interest being the assay of biological substances for human health care. Automated test equipment allows large numbers of test samples to be processed rapidly. Such equipment is employed in health care institutions including hospitals and laboratories. Biological fluids, such as whole blood, plasma or serum, are tested to find evidence of disease, to monitor therapeutic drug levels, etc.

In the automated test equipment, a sample of the test fluid is typically provided in a sample cup and all of the process steps including pipetting of the sample onto an assay test element, incubation and readout of the signal obtained are carried out automatically. The test instrument typically includes a series of work stations each of which performs one of the steps in the test procedure. The assay element may be transported from one work station to the next by various means such as a carousel to enable the test steps to be accomplished sequentially.

One type of assay element which can be used in an automated analytical is that which includes a thin porous member such as a fibrous mesh pad which is utilized as the site where the reactions(s) and/or interaction(s) occur. Such assay elements may also include reservoirs for storing reagents, mixing fluids, diluting samples, etc. The assay elements also include an opening to permit administration of a predetermined amount of a sample fluid, and if necessary any other required reagent(s), to the porous member such as by a pipette. The assay element may also include a window to allow a signal obtained as a result of the process steps, typically a fluorescent or a colorimetric change in the reagents present in the porous member, to be read such as by means of a spectrophotometer or a fluorometer included in the instrument.

The reagent reservoir(s) in such assay elements may be sealed with a frangible or puncturable thin foil layer so as to provide for a self contained element in which the requisite test reagents are carried by the element itself. The automated analytical test instrument includes the necessary pipette(s) and apparatus for positioning and operating the pipette(s) so as to transfer the sample fluid and other reagents to a mixing reservoir and/or to the porous member so as to permit the reaction(s) and/or interaction(s) upon which the assay is based to take place there. Temperature control means within the analytical test instrument allows for the incubation of the test sample at the temperature required for the assay procedure.

Of particular interest is an assay element which has a thin porous member supported within a guide defined by surfaces contiguous the porous member, the porous member extending between two chambers defined by a housing. The first chamber serves as a dispenser for fluid which is to be applied to the porous member and the second chamber serves as a collector of fluid displaced from the porous member and the guide which supports it. The dispensing chamber can be utilized to apply any fluid required in the assay to the porous member including sample fluids, reagent solutions, wash fluids, etc. During a test step wherein a fluid is applied to the porous member such as where the member is washed to remove excess unused reagent(s), the dispenser is filled with the wash fluid which then travels, via a port in the bottom of the dispenser, along the porous member thereby forcing any unused reagent(s) together with the fluid previously present from the porous member and the support guide into the collecting chamber. The porous member is on the order of about one-half a millimeter in thickness and the top and bottom surfaces of the guide which holds it in place are spaced apart about the same, or a very slightly larger, distance. These dimensions of the thin porous member and its degree of capillarity are such as to induce fluid deposited thereon to be transported throughout the member by capillary action.

A problem arises in the fluid application step(s) due to the capillary action in the transport of the fluid. It has been found that some of the fluid, upon exiting the port at the bottom of the dispenser, can propagate along an interface between a surface of the porous member and a wall of the guide contiguous that surface. This propagation appears to be due to capillary action and surface tension of some of the fluids.

This problem can be particularly acute in the case of a wash fluid which is applied to the porous member to remove excess unused reagents therefrom. Because some of the wash fluid passes along the surface of the porous member and is not available to remove excess unused reagents located within it, an inaccurate test result may be obtained.

Accordingly it is an object of this invention to provide an assay element which includes a porous member and which does not suffer from the aforementioned problem.

SUMMARY OF THE INVENTION

These and other objects and advantages are accomplished in accordance with the invention by providing an assay element which includes a porous member which serves as the site for the reactions and/or interactions which take place during the assay procedure. The porous member is arranged between guide surfaces formed by a housing, these guide surfaces providing support for the porous member. The porous member is disposed between two chambers formed by the housing, one of which includes a port in its bottom periphery and which serves as a dispenser for fluids such as sample fluids, reagent solutions, wash fluids, etc. which are applied to an end portion of the porous member. The second chamber serves as a collector for fluid and unused reagents which are removed from the porous member and the guide by the introduction therein of other fluid during the assay procedure.

The assay element may also include an opening in the housing to permit fluid access to the central portion of the porous member for the application thereto of sample fluid and other reagents. Further, the housing may also include other chambers to serve as reservoirs for the storage of test reagents, mixing of fluids or dilution of samples. The housing also may include a window below the porous member in order to allow readout, from below the assay element, of the signal obtained as a result of the assay process.

In a preferred embodiment the assay element is self-contained and includes one or more chambers which serve as reservoirs for test reagents or wash fluids, for mixing fluids or for dilution of samples. The storage reservoirs are sealed such as by a frangible or puncturable thin foil layer. Such portable, self-contained assay elements are particularly preferred since they can be transported easily and are suitable for use with automated analytical test instruments. The thin foil layers can be punctured or torn easily such as by a pipette tip and the reagents removed and delivered to the porous member.

In accordance with a critical feature of the invention the chamber which serves as a fluid dispenser for applying fluid to an end portion of the porous member and has a port in the lower surface of the chamber to permit such fluid access is provided with a ridge which extends around the periphery of the port and also downwardly into the porous member itself. The ridge ensures that the fluid will propagate into and through the porous member rather than along an interface between the upper surface of the porous member and the contiguous surface of the guide wherein the porous member resides. Generally, it is preferred to extend the ridge into the porous member approximately one-half of the distance between the top and bottom surfaces thereof. Extending the ridge into the porous member has the effect of entraining substantially all of the liquid flow within the member rather than permitting any significant amount of liquid to flow along the interface of the member and the guide surface. By providing the ridge in this manner there is provided a much more efficient fluid flow through the porous member.

In one embodiment of an immunometric sandwich assay procedure which may be practiced with the assay elements of the invention, it is necessary to apply a wash fluid via the dispenser chamber to one end portion of the porous member for the purpose of removing from the member and the guide any unused reagents together with the fluid present and/or for rendering a label present in one of the reagents detectable. Typically, the wash step requires a relatively large amount of fluid, e.g., from about 50 microliters ($\mu$l) to about 100 $\mu$l or more. By arranging the ridge around the periphery of the port of the dispenser chamber as described above, the whole volume may be dispensed into the chamber at one time and the fluid allowed to flow slowly into and through the porous member over a period of time, e.g., about 1 to 2 minutes, thereby resulting in a very efficient wash procedure. In addition, the pipette is available to carry out a process step or steps in connection with other assay elements being processed in the instrument thereby increasing the throughput of the instrument. A substantially longer dispense time would be needed if the pipette were required to remain in place to slowly dispense the wash fluid so as to ensure that it propagates into and through the porous member.

BRIEF DESCRIPTION OF THE DRAWINGS

The aforementioned aspects and other features of the invention are explained in the following description, taken in connection with the accompanying drawings wherein.

DESCRIPTION OF THE PREFERRED EMBODIMENTS

Figure 1:
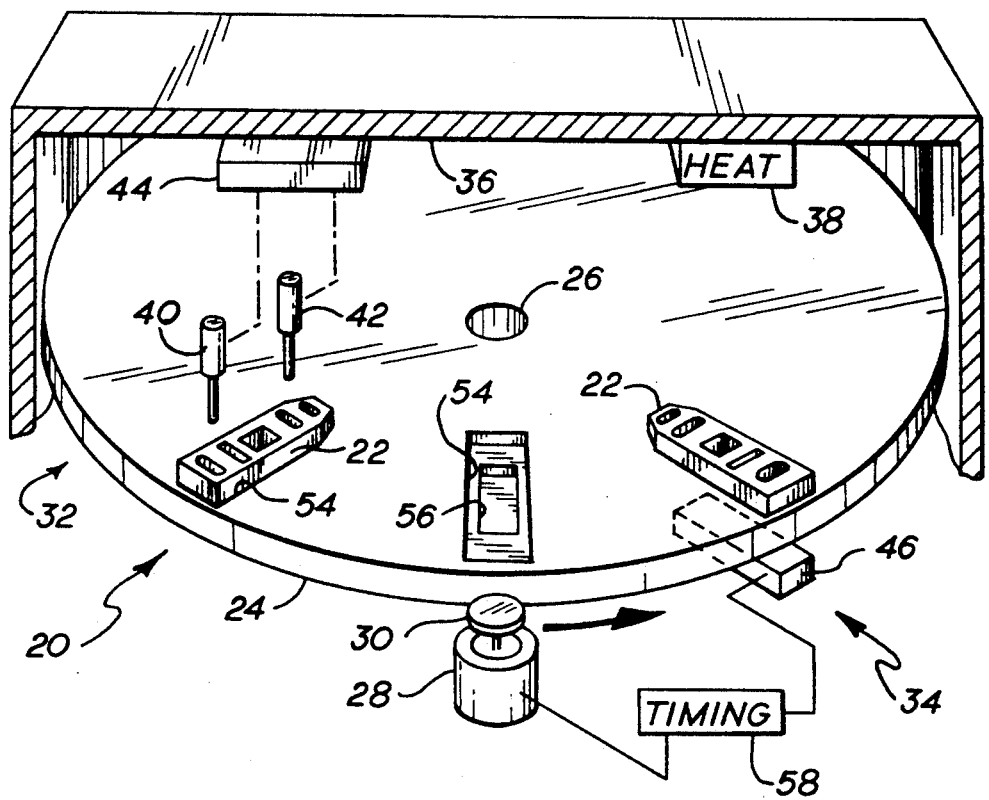
FIG. 1 is a stylized view, partially diagrammatic, of an analytical instrument employing assay elements of the invention, the instrument providing for moving the elements among various workstations and employing pipettes for administration of liquid reagents.
Figure 2:
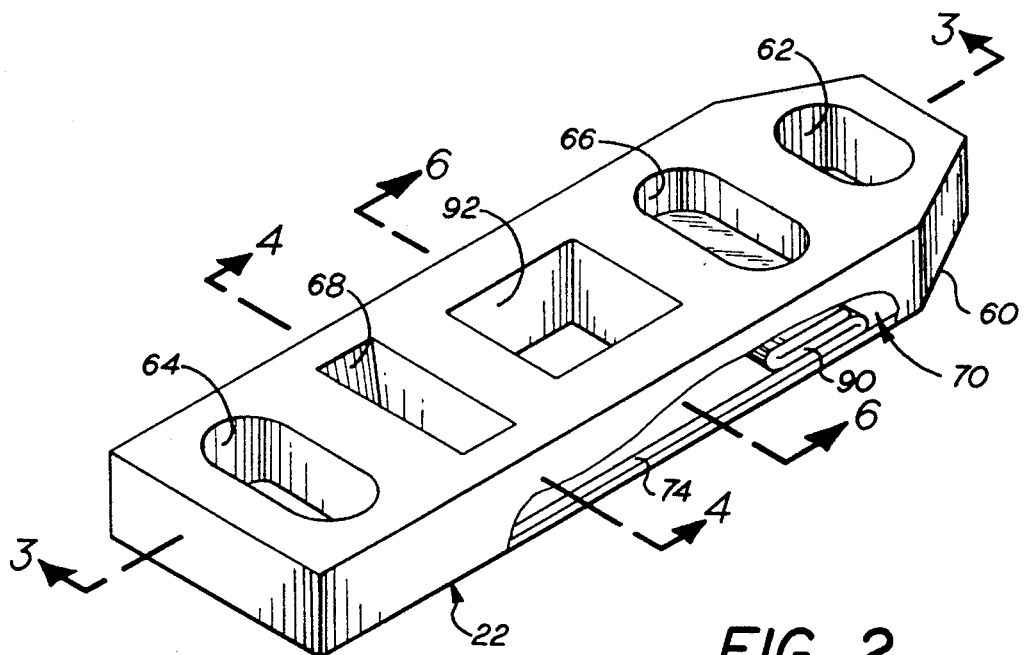
FIG. 2 is a simplified isometric view of a preferred assay element constructed in accordance with the invention, the element being employed in the instrument of FIG. 1.
Figure 3:
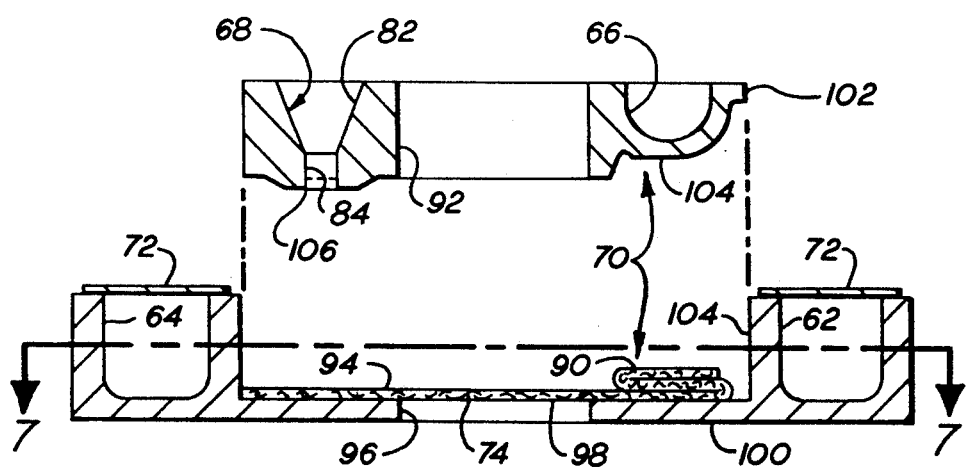
FIG. 3 is a longitudinal sectional exploded view of the assay element taken along the line 3—3 in FIG. 2.
Figure 4:
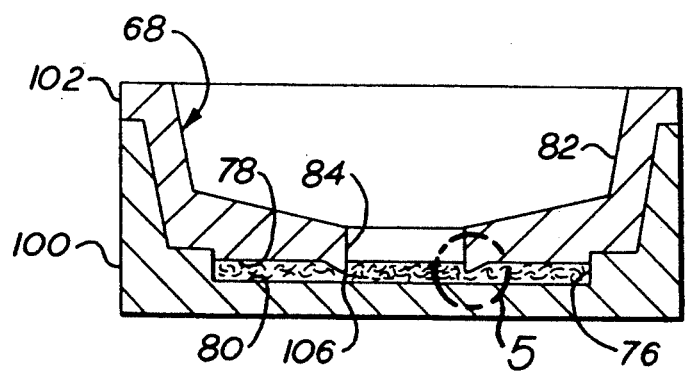
FIG. 4 is a transverse sectional view of the assay element taken along the line 4—4 in FIG. 2.

In FIG. 1 there is shown an analytical instrument 20 which provides automatically a sequence of process steps to accomplish an assay of a test sample. A plurality of assay elements 22 can be processed at the same time so as to increase the throughput rate of the instrument, one process step being carried out with one assay element concurrently with the performance of other process steps with other assay elements. The instrument 20 includes a turntable or carousel 24 which is rotated about an axle 26 by a motor 28. By way of example, the motor 28 may be mechanically coupled to the carousel 24 by a gear 30. The carousel 24 carries the assay elements 22 from one work station to another work station, two such work stations 32 and 34 being shown, by way of example, in FIG. 1. The carousel 24 rotates within a temperature controlled chamber 36 having a heater 38 for maintaining a desired temperature at the various work stations so as to allow for a process step of incubation.

Work station 32 is a pipetting station whereat sample fluid and test reagents are delivered to the assay elements 22. By way of example there are shown two pipettes 40 and 42. Preferably the pipettes are utilized with disposable pipette tips (not shown), each disposable tip being used for delivery of one fluid only and then discarded so as to avoid contamination which could lead to errors in the assay result. Pipettes 40 and 42 are positioned and operated by a pipette mechanism 44 mechanically connected to the pipettes 40 and 42 as indicated by dashed lines.

During the assay procedure, as a result of the reaction(s) and interaction(s) between the sample and the test reagent(s) which take place on the porous member, a detectable change in effected in the assay element corresponding to the presence of the analyte of interest in the sample. The detectable change can be a color change which may be read spectrophotometrically such as with a densitometer or, in an assay method based on fluorescent-labeled biologically active species or one which involves the generation of a fluorescent species as a result of a reaction between test reagents, a fluorescent output signal can be generated and read spectrofluorometrically. The detectable change can be read from above or below the assay element. At work station 34 there is shown by way of example a fluorometer 46 for irradiating the porous member of the assay element and for measuring the fluorescence emitted from the fluorescent species present therein. In the embodiment illustrated it is evident that a small aperture (not shown)

is present in carousel 24 to allow the irradiating illumination to reach the porous member and to permit the reflected fluorescent emissions to be collected and measured. It is apparent that the carousel may be arranged so as to accommodate a varying number of assay elements 22. Each position, or berth, 54 for holding cartridges 22 is provided with a small aperture 56 as described above. Operation of the motor 28, the pipette mechanism 44 and the fluorometer 46 are synchronized by means of timing unit 58.

As described above, the assay elements of the invention comprise a housing which includes a porous member arranged between a chamber having a port for dispensing fluid to one end portion of the porous member and a chamber for collecting liquid and excess unused reagents. The assay elements may also include a chamber with a port therein for permitting fluids such as sample fluid and test reagents to be delivered to the central portion of the porous member. The sample fluid and test reagents can be provided in storage cups within the analytical instrument, aspirated into a pipette 40 or 42 and delivered to the assay element at the appropriate times during the assay procedure. According to a preferred embodiment of the invention there is provided a self-contained assay element which carries all of the test reagents, except for the sample fluid, necessary for a particular assay. This preferred embodiment, shown partially in FIG. 1 and in detail in FIGS. 2–7, includes a plurality of chambers in a housing 60 of an assay element 22 wherein a first chamber serves as a front reservoir 62 for the storage of a liquid reagent to be employed in the assay, a second of the chambers serves as a back reservoir 64 for the storage of another liquid reagent for the assay, an optional third chamber serves as a mixing bowl 66 for the mixing of reagents and a fourth chamber forms a part of a dispenser 68 which is utilized to dispense a fluid to one end of the porous member 74. There is also shown a chamber 70 within the housing wherein there is arranged an absorbing material for absorbing fluid removed from the porous member and the guide such as by a wash fluid as the latter propates through the porous member because of capillary action. A frangible or puncturable foil 72 can be disposed over front reservoir 62 and back reservoir 64 for containing the liquid reagents within these reservoirs thus providing the self contained feature.

Also included in the assay element is the porous member 74 which may be any thin porous member possessing an intercommunicating network of openings throughout such that a fluid deposited on the member will propagate throughout the member because of capillary action and which is capable of retaining therein the reaction product(s) of the assay. The thin porous member may be any suitable element such as a porous membrane, a fibrous mesh pad, and the like and may be of any suitable material such as glass, polymeric materials, paper, etc. In a preferred embodiment, porous member 74 comprises a fibrous mesh pad which may be of any suitable fibrous material; a preferred material is a nonwoven glass fiber mesh, the fibers being very thin such as on the order of about 1 micrometer ($\mu$m).

The porous member 74 is mounted within a guide 76 formed within the housing 60 and having top and bottom surfaces 78 and 80, respectively, which are spaced apart a distance sufficient to support the pad 74. By way of example, the spacing between the top guide surface 78 and the bottom guide surface 80 may be in the range of from about 0.30 mm to about 0.60 mm; and preferred-spacing is about 0.4 mm.

The porous member 74 extends from the dispenser 68 to the chamber 70 which holds the absorbing material. The dispenser chamber 68 is configured as a well 82 for holding a fluid, the dispenser 68 including a port 84 at the bottom of well 82 for allowing communication of fluid from well 82 into the porous member 74. The port 84 is disposed about a longitudinal center line of the porous member 74 and extends only part of the way to each of the side edges 86 and 88 thereof. Liquid absorbing material 90, which may be any suitable material, is located within chamber 70 and forms a part of the chamber 80 for taking up fluid expelled from the guide and the porous member. Absorbing material 90 is located contiguous porous member 74 and in a preferred embodiment is formed conveniently as an extension of the porous material folded back and forth on itself.

The housing 60 also preferably includes a chamber 92 which is positioned immediately above the top horizontal surface 94 of the porous member 74 and has a port at the bottom periphery thereof to allow fluid to be delivered to the porous member 74. The housing 60 also may include a transparent window portion 96 positioned immediately below the bottom surface 98 of the pad 74 to provide access for the light used to measure the detectable change effected in the porous member as a result of the assay process. In a preferred embodiment the housing 60 includes an opening in the area shown as the transparent window 96 to permit the light to be directed onto the porous member without having to pass through the material of which the housing 60 is comprised. Both chamber 92 and transparent window 96 are provided with a rectangular shape in the preferred embodiment of the invention although different shapes such as round or elliptical may be utilized for the window or opening. Also, chamber 92 and window 96 are constructed with the same dimensions according to a preferred embodiment; however, if desired, they may be provided in different sizes. Chamber 92 and window 96 generally are located about midway between the dispenser 68 and the absorber chamber 70.

As a convenience in assembly of the element 22, the housing 60 is formed initially of a lower portion in the form of a boat 100 and an upper portion which is formed as an insert 102 to be inserted in the boat 100. Both the boat 100 and the insert 102 are preferably fabricated of a polymeric material which is inert to the reagents employed by the system 20. Any suitable polymeric material may be used for construction of the boat 100 and the insert 102. In the construction of the element 22, the porous member 74 and the absorbing material 90 are inserted into their positions within the boat 100, after which the insert 102 is emplaced above the porous member 74 in the boat 100 and secured to the boat 100 as by ultrasonic welding. The insert 102 includes the well 82 of the dispenser 68 and a chamber which serves as a hold 104 of the absorber 70 for securing the absorbing material 90 in the absorber 70. The chamber 92 is also formed within the insert 102. The reservoirs 62 and 64, the mixing bowl 66, and the bottom window 96 are formed within the boat 100.

In accordance with an important feature of the invention, the port 84 is provided with a ridge 106 which extends completely around a perimeter of the port 84 and, furthermore, protrudes downward into the porous member 74 a distance equal to approximately one-half the thickness of the member 74. The protrusion of the ridge 106 into the porous member 74 introduces a localized compression of the member 74 which results in a directing of fluid from the dispenser 68 to flow throughout the porous member 74 by capillary action, and inhibit a flowing of the fluid along an interface between the surfaces of the porous member 74 and the surfaces of the guide 76.

Figure 5:
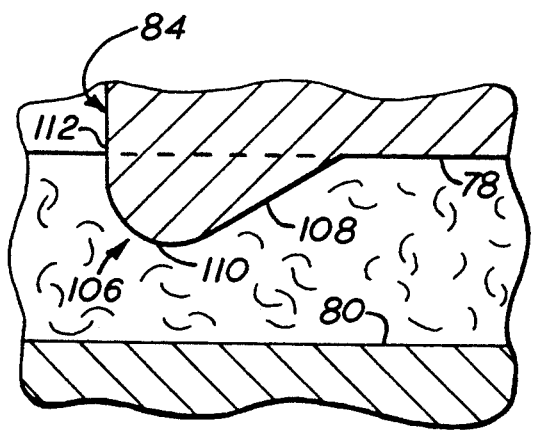
FIG. 5 is an enlarged detailed view of a ridge in the dispenser port of FIGS. 3 and 4.
Figure 6:
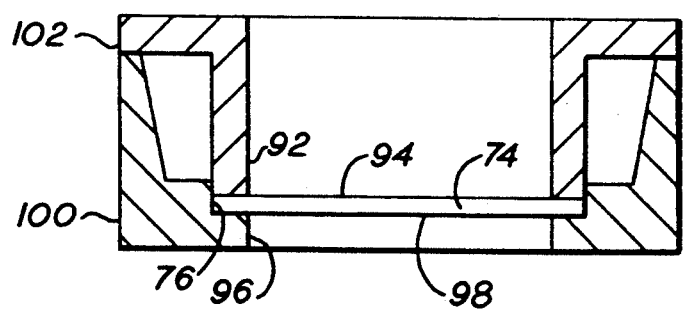
FIG. 6 is a transverse sectional view of the assay element taken along the line 6—6 in FIG. 2.
Figure 7:
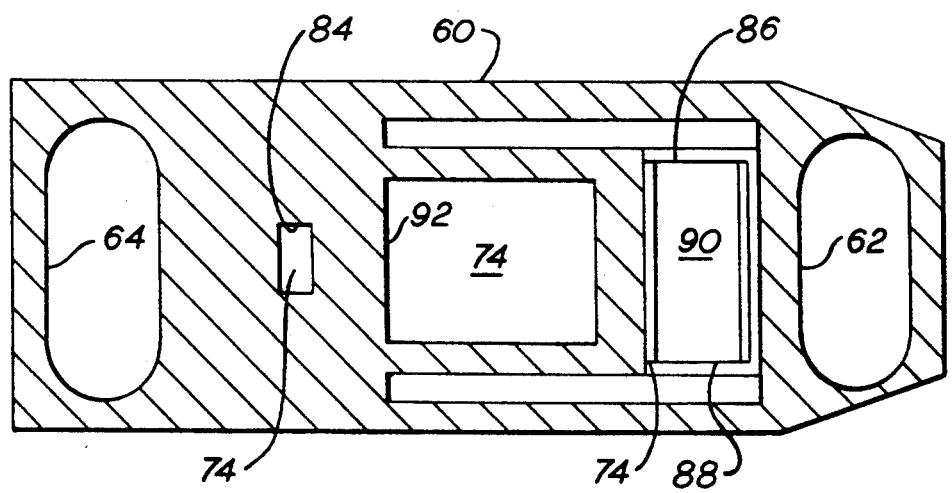
FIG. 7 is a sectional view of the assay element taken along the line 7—7 in FIG. 3, the view of FIG. 7 showing in a horizontal plane a top surface of a porous member and the locations of a dispenser port, an opening in the top of the housing and an absorber of the element in relation to the porous member.

In the operation of the element 22, fluid is drawn into the porous member 74 from the dispenser 68 by capillary action. The porous member, e.g., the fibrous mesh pad, serves to regulate the flow of fluid under the capillary forces to provide a uniform smooth flow which precludes any development of air bubbles, and insures a uniform distribution of fluid in the porous member 74. The configuration of the ridge 106, as viewed in cross section, shown in FIG. 5, provides that the side of the ridge facing the port 84 extends directly downward into the porous member 74. The side of the ridge facing away from the port 84 is provided with a taper 108 which extends from a tip 110 of the ridge 106 back to the top guide surface 78. The tip 110 is rounded. In a preferred embodiment of the invention, the intersection of the taper 108 with the top guide surface 78 is at a distance of approximately 0.50 mm from an edge 112 of the port 84; the protrusion of the tip 110 beyond the top guide surface 78 is about 0.20 mm; inclination of the taper 108 relative to the top guide surface 78 is at an angle of approximately 30 degrees; and rounding of the tip 110 is accomplished with a radius of curvature having a maximum value of approximately 0.125 mm.

By way of illustration the typical dimensions used in a preferred embodiment of the assay element 22 will be given, it being understood that these can be varied as desired. The port 84 can be about 2 mm in the longitudinal direction of the element 22, and about 3 mm in the transverse direction perpendicular to the center line of the porous member 74. The port 84 has been illustrated with a rectangular shape, however another shape such as a circular shape or elliptical shape may be employed. The chamber 92 and window 96 can measure about 9 mm in the longitudinal direction and about 7.5 mm in the transverse direction. The insert 102 can measure about 23 mm in the longitudinal direction and about 15 mm in the transverse direction. The width of the porous member 74 is approximately equal to the width of the insert 102. The height of the insert 102 can be about 6.5 mm.

Although the assay element of the invention is preferably utilized for the analysis of biological fluids such as plasma, serum, etc., it should be understood that the element may be used to carry out analyses of other fluids. In a preferred embodiment the assay cartridge is employed to carry out immunometric assays for an analyte, e.g., an antigen or an antibody. Any of the known immunometric sandwich or competitive assays can be carried out with the assay element. Such assays are well known to those skilled in the art and extensive discussion thereof is not required here. By way of illustration the use of the assay element in conjunction with a sandwich assay for an antigen of interest will be described. In this assay an antibody raised against the antigen of interest is initially applied to the porous member 74 and immobilized therein prior to the pad being incorporated into the assay cartridge 22. Application of the antibodies to the porous member and immobilization of the antibodies therein can be accomplished by any of various known techniques. For example, a fluid containing the antibodies can be applied to the porous member and the member subsequently dried to provide a porous member having the antibodies distributed throughout and held therein by the structure of the member. In other embodiments, particularly where the porous member comprises a fibrous mesh material, antibodies can be chemically bound to polymeric particles and the fibrous mesh impregnated with the particulate matter or the fibrous mesh pad can be impregnated with an immunocomplex of the antibodies. In this manner the antibodies are immobilized in the fibrous pad and remain therein throughout the assay process.

In the assay process a volume of sample fluid, typically 20–30 μl, is aspirated into a pipette from a sample cup and deposited on the porous member 74 through chamber 92 while the assay element 22 resides on the carousel 24. The sample fluid is drawn throughout the porous member via capillary action and the assay element is allowed to incubate for a suitable period at the appropriate temperature to allow the sample antigen to interact with the immobilized antibodies dispersed throughout the member. Subsequently, foil 72, which is secured about the mouth of reservoir 62 to form a seal over a solution of an enzyme-linked antibody (an antibody directed to the same antigen as that immobilized in the porous member), is perforated by means of a pipette, 40 or 42, carrying a disposable tip and a desired volume of the enzyme-linked antibody solution, typically 10–20 μl, is aspirated into the pipette tip. The solution is then deposited onto porous member 74 through chamber 92 and drawn throughout the member by capillary action. The assay element 22 is again allowed to incubate to permit the interactions between the enzyme-linked antibodies and the sample antigen to occur thus forming the ternary complex with the immobilized antibodies and the sample antigens. Since the enzyme label must be detected indirectly, a desired volume, typically 50–100 μl, of a solution of a substrate for the enzyme is applied to the porous member. This is accomplished by piercing the foil 72 of reservoir 64 with a disposable pipette tip carried by pipette 40 or 42 and aspirating the desired volume into the pipette tip. This substrate solution is utilized both as a wash fluid to remove from the porous member and the guide area any unbound sample antigen and enzyme-linked antibodies and to render the enzyme label detectable. The substrate solution is deposited into the well 82 of dispenser 68. The substrate solution exits the well 82 via the port 84 and is guided into the porous membrane 74 by ridge 106. As the substrate solution propagates through the porous membrane 74 it forces any unbound sample antigen and enzyme-linked antibody together with the fluid out of the porous member and into the absorber chamber 70 where they are taken up by absorber material 90. The duration of this step is approximately 1–2 minutes. The signal provided by the fluorescent species liberated by the reaction of the enzyme with the substrate material is read by means of the fluorometer 46.

It will, of course, be evident that the assay process described above can be modified by utilizing a separate wash fluid such as water to replace the fluid in the porous member and guide area and to remove unbound antigens and enzyme-linked antibodies. In this procedure the substrate solution is applied to the porous member after the wash fluid.

Although the invention has been described with respect to a specific preferred embodiment it is evident that this is illustrative only and other embodiments of the invention will be apparent to those skilled in the art.

For example, a ridge such as that illustrated at 106 around the bottom periphery of port 84 can be provided around the bottom periphery of chamber 92 if desired. Further any number of reservoirs for holding reagents, diluting samples or mixing samples and/or reagents can be provided in the assay element.

What is claimed is:

1. An assay element comprising a housing including a porous member arranged between top and bottom guide surfaces,
   a chamber for dispensing fluid to an end portion of said porous member and a chamber for receiving fluid which leaves said porous member, said fluid dispensing chamber and said fluid receiving chamber being disposed contiguous opposed ends of said porous member,
   wherein said fluid dispensing chamber includes a well having a port in the bottom thereof contiguous said porous member and opening to said porous member for conducting fluid from said well to said porous member; and
   a ridge encircling the perimeter of said port and protruding into and compressing said porous member for entraining fluid from said fluid dispensing chamber to propagate into and within said porous member.

2. The assay element according to claim 1 wherein said porous member comprises a fibrous mesh material.

3. The assay element according to claim 2 wherein said fibrous mesh material has a thickness of from about 0.5 μm to about 2.5 μm.

4. The assay element according to claim 3 wherein said fibrous mesh material comprises nonwoven glass fibers.

5. The assay element according to claim 2 wherein said porous member has a longitudinal dimension extending from said fluid dispensing chamber to said fluid receiving chamber, said porous member having a transverse dimension lying in a plane of said port and extending perpendicular to said longitudinal dimension; and wherein a diameter of said port is smaller than said longitudinal dimension and smaller than said transverse dimension.

6. The assay element according to claim 5 wherein said port is symmetrically positioned on a center line of said porous member, said center line extending parallel to said longitudinal dimension.

7. The assay element according to claim 1 wherein said ridge has a taper on a side thereof away from said port, the taper extending to one of said guide surfaces.

8. The assay element according to claim 1 wherein a side of said ridge facing said port extends directly into said porous member, said ridge having a taper of a side thereof facing away from said port, said taper extending to one of said guide surfaces; and wherein
   said ridge has a depth of penetration into said porous member measured from said one guide surface, said ridge having a width measured from an edge of said port to an intersection of said taper with said one surface, said ridge width being larger than said depth of penetration by a factor of approximately 2.5.

9. The assay element according to claim 8 wherein the width of said ridge is approximately 0.55 mm, the penetration depth of said ridge is approximately 0.2 mm, said taper has an angle of approximately 30 degrees measured relative to said one guide surface, and wherein a tip portion of said ridge is rounded.

10. The assay element according to claim 8 wherein said port has a rectangular shape.

11. The assay element according to claim 1 and further comprising
    an opening disposed in said housing above a central portion of said porous member.

12. The assay element according to claim 11 and further including at least one reservoir integrally formed within said housing for storing fluid reagent required for an assay.

13. The assay element according to claim 12 and further including a reservoir integrally formed in said housing for mixing fluid reagents and/or a fluid sample required for said assay.

14. The assay element according to claim 11 and further including a window disposed in said housing contiguous the bottom surface of said porous member, said window permitting electromagnetic radiation to be directed onto said porous member.

15. The assay element according to claim 11 and further including an opening disposed in said housing contiguous the bottom surface of said porous member.

16. The assay element according to claim 11 wherein said fluid receiving chamber disposed contiguous one end of said porous member includes a fluid absorbing material disposed in said chamber contiguous said porous member.

17. The assay element according to claim 16 wherein a side of said ridge facing said port extends directly into the porous member, said ridge having a taper of a side thereof facing away from said port, said taper extending to one of said guide surfaces; and wherein said ridge has a depth of penetration into the porous member measured from said one guide surface, said ridge having a width measured from an edge of said port to an intersection of said taper within said one surface, said ridge width being larger than said depth of penetration by a factor of approximately 2.5.

18. The assay element according to claim 17 wherein said guide surfaces define a guide enclosing said porous member and extending longitudinally along said porous member, said guide having a depth, as measured in a direction perpendicular to the plane of said port, in the range of from about 0.08 mm to about 0.14 mm.

19. The assay element according to claim 1 wherein said fluid receiving chamber disposed contiguous one end of said porous member includes a fluid absorbing material disposed in said chamber contiguous said porous member.

20. The assay element according to claim 1 wherein said ridge protrudes into said porous member about one-half of the distance between the top and bottom surfaces thereof.

* * * * *